United States Patent [19]

Bossert et al.

[11] 4,048,171
[45] Sept. 13, 1977

[54] 1,4-DIHYDROPYRIDINES

[75] Inventors: Friedrich Bossert, Wuppertal-Elberfeld; Wulf Vater, Opladen, both of Germany

[73] Assignee: Bayer Aktiengesellschaft, Germany

[21] Appl. No.: 113,038

[22] Filed: Feb. 5, 1971

[30] Foreign Application Priority Data

Feb. 5, 1970 Germany .............................. 2005116

[51] Int. Cl.² .......................................... C07D 211/84
[52] U.S. Cl. .................... 260/256.4 C; 260/294.8 D; 424/251; 424/263; 260/295.5 R;294.8 C;294.8 D;256.4 C;295.5 B; 260/295.5 B; 260/294.8 C
[58] Field of Search ................. 260/295.5 R, 294.8 C, 260/294.8 D, 256.4 C, 295.5 B

[56] References Cited
U.S. PATENT DOCUMENTS

| | | | |
|---|---|---|---|
| 3,325,505 | 6/1967 | Loev .............................. | 260/295.5 R |
| 3,441,648 | 4/1969 | Loev .............................. | 260/295.5 R |
| 3,455,945 | 7/1969 | Loev .............................. | 260/295.5 R |
| 3,485,847 | 12/1969 | Bossert et al. ................. | 260/295.5 R |
| 3,488,359 | 1/1970 | Bossert et al. ................. | 260/295.5 R |
| 3,511,847 | 5/1970 | Loev et al. ..................... | 260/295.5 R |
| 3,647,807 | 3/1972 | Bossert et al. ................. | 260/295.5 R |
| 3,691,177 | 9/1972 | Bossert et al. ................. | 260/295.5 R |
| 3,696,112 | 10/1972 | Bossert et al. ................. | 260/295.5 R |
| 3,708,489 | 1/1973 | Rucker et al. ................. | 260/295.5 R |

FOREIGN PATENT DOCUMENTS

| | | | |
|---|---|---|---|
| 2,025,618 | 12/1969 | France ......................... | 260/295.5 R |
| 1,813,436 | 10/1970 | Germany ..................... | 260/295.59 |

OTHER PUBLICATIONS

"J. Org. Chem. USSR" Blokhin et al. vol. 39 No. 7, pp. 1592-1595 (1969).

Phillips, "J. Am. Chem. Soc." vol. 71, pp. 4003-4007 (1949).

Primary Examiner—Henry R. Jiles
Assistant Examiner—Robert T. Bond
Attorney, Agent, or Firm—Jacobs & Jacobs

[57] ABSTRACT

1,4-Dihydropyridines of the formula:

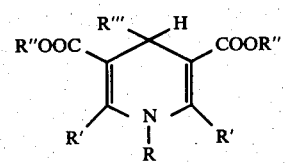

wherein
R is hydrogen, straight, branched or cyclic lower alkyl, lower alkenyl, or lower alkinyl, unsubstituted or substituted; or benzyl, or phenethyl, unsubstituted or substituted in the aryl portion;
R' is alkyl of 1 to 4 carbon atoms;
R" is alkenyl of 2 to 6 carbon atoms, alkinyl of 2 to 6 carbon atoms, cyclic alkenyl of 3 to 6 carbon atoms interrupted by oxygen, alkenyl of 2 to 6 carbon atoms or alkinyl of 2 to 6 carbon atoms interrupted by 1 or 2 oxygen atoms, or alkenyl of 2 to 6 carbon atoms or alkinyl of 2 to 6 carbon atoms substituted by hydroxyl; and
R'" is unsubstituted or substituted aryl; cyclohexyl; benzyl; styryl; pyridyl; pyrimidyl; furyl; thienyl; pyrrolyl; pyridyl, pyrrolyl, thienyl or furyl substituted by alkyl of 1 or 2 carbon atoms; or substituted pyrimidyl:
are useful for their coronary dilating effect, their nitrite-like effect on the heart, their anti-fibrillation effect, their vascular-spasmolytic effect and muscular-spasmolytic effect, and as anti-hypertensives.

39 Claims, No Drawings

1,4-DIHYDROPYRIDINES

The present invention is concerned with 1,4-dihydropyridines, processes for their production, pharmaceutical compositions embodying said 1,4-dihydropyridines as the active ingredient and methods of administration which utilize the administration of said 1,4-dihydropyridines orally, parenterally or perlingually.

More particularly, the present invention relates to 1,4-dihydropyridines of the formula:

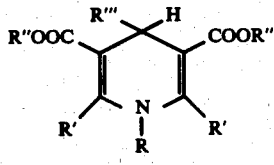

wherein
R is hydrogen, straight, branched or cyclic lower alkyl, lower alkenyl, or lower alkinyl, unsubstituted or substituted by hydroxyl or alkoxy of 1 to 3 carbon atoms; or benzyl, or phenethyl, unsubstituted or substituted in the aryl portion by 1 to 3 members selected from the group consisting of 1 to 3 alkoxy moieties of 1 to 3 carbon atoms, 1 or 2 alkyl moieties of 1 to 3 carbon atoms, and 1 or 2 halogen atoms;
R' is straight or branched chain alkyl of 1 to 4 carbon atoms;
R" is straight or branched chain alkenyl of 2 to 6 carbon atoms, straight or branched chain alkinyl of 2 to 6 carbon atoms, cyclic alkenyl to 3 to 6 carbon atoms interrupted by oxygen, straight or branched chain alkenyl of 2 to 6 carbon atoms or alkinyl of 2 to 6 carbon atoms interrupted by 1 or 2 oxygen atoms, or straight or branched chain alkenyl of 2 to 6 carbon atoms or alkinyl of 2 to 6 carbon atoms substituted by hydroxyl; and R''' is aryl, unsubstituted or substituted by 1 to 3 members selected from the group consisting of 1 to 3 nitro moieties, 1 to 3 halogen atoms, 1 to 2 hydroxyl moieties, 1 or 2 acyloxy moieties of 1 or 2 carbon atoms in the acyl portion, 1 to 3 alkoxy moieties of 1 to 4 carbon atoms, 1 or 2 dihydroxymethylene moieties, 1 or 2 amino moieties, 1 or 2 acylamino moieties of 1 or 2 carbon atoms in the acyl portion, trifluoromethyl, carboxy and carbalkoxy of 1 to 4 carbon atoms in the alkoxy portion; cyclohexyl; benzyl; styryl; pyridyl; pyrimidyl; furyl; thienyl; pyrrolyl; pyridyl, pyrrolyl, thienyl or furyl substituted by alkyl of 1 or 2 carbon atoms; or pyrimidyl substituted by at least one member selected from the group consisting of alkyl of 1 or 2 carbon atoms, 1 or 2 methoxy moieties, 1 or 2 ethoxy moieties and a dioxymethylene group of the formula:

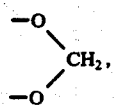

These compounds are useful as coronary dilators, for their nitrite-like effect on the heart, as anti-fibrillation agents, for their vascular-spasmolytic and muscular-spasmolytic effect, and as anti-hypertensives.

The compounds of the present invention may be produced by reacting an aldehyde of the formula:

wherein R''' is as above defined, either (a) with an acyl-fatty acid ester of the formula:

wherein R' and R" are as above defined, with ammonia or an amine of the formula:

wherein R is as above defined, or a salt thereof, or (b) with an amine of the formula:

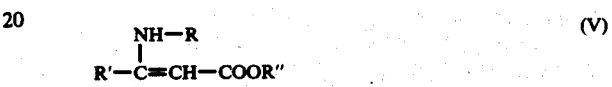

wherein R, R' and R" are as above defined, at an elevated temperature preferably from about 70° C to about 120° C in the presence of at least one organic solvent, such as an alcohol, glacial acetic acid, dioxane, dimethylformamide, dimethylsulphoxide, acetonitrile or water. When an organic solvent is used, it is preferred to carry out the reaction at approximately the boiling point of the solvent or of the solvent mixture.

When R in formula (I) above is other than hydrogen, the compounds of the present invention may be produced according to a process carried out in the presence of pyridine, which process is set forth in co-pending U.S. application Ser. No. 35,574, filed May 7, 1970 (German P 19 23 990.8).

An alternate procedure for producing compounds of the present invention is described in Helv. chim. Acta 41 (1958) 2066 wherein when the compound of formula (I) have R as hydrogen, 1,4-dihydropyridines are oxidized with suitable oxidizing agents, the resulting pyridine derivatives are quaternized with alkyl esters, and these esters are reduced to the corresponding 1,4-dihydropyridines with suitable reducing agents.

Suitable reactants for use in the processes of the present invention and for the production of the compounds of the present invention include as illustrative examples the following:

Aldehydes

Benzeldehyde, 2-, 3- or 4-hydroxybenzaldehyde, 2,4- or 2,6-dihydroxybenzaldehyde, 2-, 3- or 4-methoxybenzaldehyde, 2-isopropoxybenzaldehyde, 3-butoxybenzaldehyde, 3,4-dioxymethylenebenzaldehyde, 3,4,5-trimethoxybenzaldehyde, 2-, 3- or 4-chloro or bromo or fluorobenzaldehyde, 2,4- or 2,6-dichlorobenzaldehyde, 2,4-dimethylbenzaldehyde, 3,5-diisopropyl-4-hydroxybenzaldehyde, 2-, 3- or 4-nitrobenzaldehyde, 2,4- or 2,6-dinitrobenzaldehyde, 2-nitro-6-bromobenzaldehyde, 2-nitro-3-methoxy-6-6-chlorobenzaldehyde, 2-nitro-4-chlorobenzaldehyde, 2-nitro-4-methoxybenzaldehyde, 2-, 3-or 4-trifluoromethylbenzaldehyde, benzaldehyde-2-(3- or 4-) carboxylic acid, benzaldehyde-2-carboxylic acid ethyl ester, benzaldehyde-3-carboxylic acid isopropyl ester, benzaldehyde-4-carboxylic acid butyl ester, 2-nitrobenzaldehyde-4-carboxylic acid, 3-nitrobenzaldehyde-4-carboxylic acid ethyl ester, cinnamaldehyde, hydrocinnamaldehyde, formylcyclohexane, 1-formyl-cyclohexene-3, 1-formyl-cyclohexine-1,3, 1-formylcyclopentene-3, α,β- or γ-pyridinaldehyde, 6-methylpyridine-2-aldehyde, pyrimidine-5-aldehyde, 4,6-dimethoxy-pyrimidine-5-aldehyde, furan-2-aldehyde, thiophen-2-aldehyde and pyrrol-2-aldehyde.

Esters

Acetoacetic acid alkyl ester, acetoacetic acid ($\alpha',\alpha'$-dimethyl)-alkyl ester, acetoacetic acid-propargyl ester, acetoacetic acid ($\alpha',\alpha'$-dimethyl)-propargyl ester, acetoacetic acid furfuryl ester, acetoacetic acid γ-hydroxyalkyl ester, acetoacetic acid γ-hydroxy-propargyl ester.

Amines

Methylamine, ethylamine, propylamine, isopropylamine, butylamine, allylamine, propargylamine, 1-hydroxyethylamine-2,1,3-dihydroisopropylamine, cyclohexylamine, benzylamine, 4-chlorobenzylamine, 3,4-dimethoxybenzylamine and phenethylamine.

According to a preferred embodiment of the present invention R is hydrogen, alkyl of 1 to 6 carbon atoms, benzyl or phenethyl, R' is straight or branched chain alkyl of 1 to 4 carbon atoms, R" is alkenyl of 2 to 6 carbon atoms, alkinyl of 2 to 6 carbon atoms, alkenyl of b 2 to 6 carbon atoms or alkinyl of 2 to 6 carbon atoms interrupted by oxygen, or cyclic alkenyl of 3 to 6 carbon atoms wherein the ring contains oxygen as a heteroatom, and R''' is cyclohexyl; benzyl; phenyl unsubstituted or substituted by 1 to 3 members selected from the group consisting of 1 to 3 nitro moieties, 1 to 3 halogen atoms especially fluorine, chlorine or bromine, 1 or 2 hydroxy moieties, 1 to 3 alkoxy moieties of 1 to 4 carbon atoms, 1 or 2 hydroxymethylene moieties, carbalkoxy of 1 to 4 carbon atoms, carboxy and trifluoromethyl; pyridyl, pyrrolyl, or thienyl unsubstituted or substituted by alkyl of 1 or 2 carbon atoms; or pyrimidyl unsubstituted or substituted by alkyl of 1 or 2 carbon atoms, 1 or 2 methoxy moieties, 1 or 2 ethoxy moieties or 1 or 2 hydroxymethylene moieties.

According to a particularly preferred embodiment, R is hydrogen, alkyl of 1 to 4 carbon atoms or benzyl, R' is alkyl of 1 to 4 carbon atoms, R" is alkenyl of 3 to 4 carbon atoms, alkinyl of 3 or 4 carbon atoms or furfuryl, and R''' is cyclohexyl; phenyl unsubstituted or substituted by 1 to 3 groups selected from the group consisting of nitro, chlorine, bromine, 1 to 3 methoxy moieties, trifluoromethyl, carbomethoxy, carboxy and 1 or 2 hydroxymethylene moieties; pyridyl; thienyl; pyrrolyl; N-methylpyrrolyl; or dimethoxypyrimidyl.

The 1,4-dihydropyridines of the present invention have a broad range of utility as indicated above and the following effects have been exhibited in animal experiments:

1. The compounds produce a distinct and long-lasting dilation of the coronary vessels on parenteral, oral and perlingual administration. This action on the coronary vessels is intensified by a simultaneous, nitrite-like effect of reducing the load on the heart. They influence or modify the heart metabolism in the sense of a saving of energy.

2. The excitability of the stimulus-forming and stimulus-conducting system within the heart is lowered, so that an anti-fibrillation action, demonstrable in therapeutic doses, results.

3. The tone of the smooth muscles of the vessels is greatly reduced under the action of the compounds. This vascular-spasmolytic action can occur in the whole vascular system or can manifest itself to a more or less isolated extent in circumscribed vascular regions (such as for example the central-nervous system).

4. The compounds reduce the blood pressure of normal tonic and hypertonic animals and can thus be used as anti-hypertensive agents.

5. The compounds have strong muscular-spasmolytic actions, which manifest themselves on the smooth muscle of the gastro-intestinal tract, the urogenital tract, and the respiratory system.

According to the present invention, pharmaceutical compositions are produced which comprise a compound of the present invention or more than one compound of the present invention in combination with a pharmaceutically acceptable non-toxic inert diluent or carrier. The present invention further includes a medicament in unit dosage form which comprises a compound of the present invention or more than one compound of the present invention per se or in combination with a pharmaceutically acceptable non-toxic inert diluent or carrier. The medicament may include a protective envelope containing the active compound or compounds, and if present, the pharmaceutically acceptable non-toxic inert diluent or carrier.

The term "medicament in unit dosage form" as used above means a medicament as defined above in the form of discrete portions each containing a unit dosage, or a multiple or sub-multiple of a unit dose of the active compound or compounds, for example two, three or four unit doses or a half, a third or a fourth of a unit dose. Such portions may, for example, be in monolithic coherent form, such as tablets, suppositories, pills or dragees; in wrapped or concealed form, such as wrapped powders, cachets, sachets or capsules; in ampoules, either free or as a sterile solution suitable for parenteral injection; or in any other form known to the art.

The 1,4-dihydropyrdines of the formula (I) can be administered orally or parenterally.

In general, it has proved advantageous to administer amounts of about 0.01 mg to about 100 mg, preferably about 0.1 to 50 mg per kg body weight per day, in order to achieve satisfactory results. Nevertheless, it may sometimes be necessary to deviate from the above ranges, depending on the body weight of the treated person or the method of application. In some cases it may be sufficient to use less than the minimum amount stated above, whereas in other cases the aforesaid upper limit will have to be exceeded. If larger amounts are applied, it may be advisable to distribute these in several individual doses over the day.

The compounds of the formula (I) can be administered as such or as pharmaceutical compositions as described above. Suitable forms of application in combination with various inert carriers are: tablets, capsules, dragees, ampoules, powders, sprays, aqueous suspensions, injectable solutions, elixirs, syrups and the like. Such carriers comprise solid diluents or fillers, a sterile aqueous medium as well as various non-toxic organic solvents and the like. Tablets and the like intended or oral application may, of course, be provided with sweetening additives and similar substances. In the aforesaid case the therapeutically active compound should be present at a concentration of about 0.5 to 90 percent by weight of the total mixture, in quantities which are sufficient to achieve the range of dosage, mentioned above.

In the case of oral administration, the tablets or capsules may also contain additives, such as sodium citrate, calcium carbonate and dicalcium phosphate together with various other additives, such as starch, preferably potato starch, and the like, and binding agents, such as polyvinyl-pyrrolidone, gelatin and the like. Lubricants, such as magnesium stearate, sodium lauryl sulphate and talc may also be added for the production of tablets. In the case of aqueous suspensions and/or elixirs which are intended for oral application, the active substance may be used with various flavouring agents, coloring substances; emulsifiers and/or together with diluents, such as water, ethanol, propylene glycol, glycerol and similar compounds or combinations of this type.

In the case of parenteral administration, solutions of the active substances in sesame or peanut oil or in aqueous propylene glycol or N,N-dimethyl formamide can be used, as can sterile aqueous solutions in the case of the water-soluble compounds. Aqueous solutions of this type should be buffered in the usual way, when required, and the liquid diluent should previously be rendered isotonic by the addition of the necessary amount of salt or glucose. These aqueous solutions are particularly suitable for intravenous and intraperitoneal injections. Sterile aqueous media of this type may be prepared in a manner per se known.

The 1,4-dihydropyridines of the present invention are particularly useful because they are suitable for oral administration. Therefore, pharmaceutical compositions in orally administrable form are the preferred embodiment of the pharmaceutical compositions.

The following non-limitative examples more particularly illustrate the present invention.

EXAMPLE 1

2,6-Dimethyl-4-(α-pyridyl)-1,4-dihydropyridine-3,5-dicarboxylic acid diallyl ester 10 cc pyridine-2-aldehyde are heated with 30 g acetoacetic acid allyl ester (b.p. 52° C/0.08 mm Hg) and 10 cc ammonia in 250 cc methanol at boiling temperature for several hours; the mixture is filtered after the addition of charcoal and, after cooling and filtering off with suction, there are obtained, 17 g of white crystals of m.p. 172° C (methanol).

EXAMPLE 2

2,6-Dimethyl-4-(α-pyridyl)-1,4-dihydropyridine-3,5-dicarboxylic acid dipropargyl ester After boiling 10 cc pyridine-2-aldehyde, 30 g acetoacetic acid propargyl ester (b.p. 63° C/0.2 mm Hg) and 10 cc ammonia in 250 cc methanol for several hours, there are obtained 13 g of white crystals of m.p. 172° C.

EXAMPLE 3

1,2,6-trimethyl-4-(β-pyridyl)-1,4-dihydropyridine-3,5-dicarboxylic acid diallyl ester 10 cc pyridine-3-aldehyde are heated together with 30 g acetoacetic acid allyl ester and 8 g methylamine hydrochloride in 50 cc pyridine at 90° to 100° C for 2 to 3 hours. The solution is subsequently poured into water, filtered off with suction and, after drying, there are obtained 18 g of white crystals of m.p. 90° C (benzene/ligroin).

The following compounds were prepared in an analogous manner from the reactants specified:

a. 1,2,6-trimethyl-4-(α-pyridyl)-1,4-dihydropyridine-3,5-dicarboxylic acid diallyl ester, m.p. 105° C; from pyridine-2-aldehyde, acetoacetic acid allyl ester and methylamine hydrochloride.

b. 1,2,6-trimethyl-4-(α-pyridyl)-1,4-dihydropyridine-3,5-dicarboxylic acid dipropargyl ester, m.p. 132° C; from pyridine-2-aldehyde, acetoacetic acid propargyl ester and methylamine hydrochloride.

EXAMPLE 4

2,6-dimethyl-4-dihydropyridine-3,5-dicarboxylic acid dipropargyl ester 10 g benzaldehyde, 28 acetoacetic acid propargyl ester and 10 cc ammonia are heated in 150 cc alcohol at boiling temperature overnight, the mixture is filtered after the addition of charcoal and, after cooling and filtering off with suction, there are obtained white-yellow crystals of m.p. 141° C (12 g; methanol).

The following compounds were prepared in an analogous manner from the reactants specified:

a. 2,6-dimethyl-4-(3'-trifluoromethylphenyl)-1,4-dihydropyridine-3,5-dicarboxylic acid diallyl ester, m.p. 104° C; from 3-trifluoromethylbenzaldehyde, acetoacetic acid allyl ester and ammonia.

2,6-dimethyl-4-(3'-nitrophenyl)-1,4-dihydropyridine-3,5-dicarboxylic acid dipropargyl ester, m.p. 136° C; from 3,-nitrobenzaldehyde, acetoacetic acid propargyl ester and ammonia.

2,6-dimethyl-4-(3'-nitro-6'-chlorophenyl)-1,4-dihydropyridine-3,5-dicarboxylic acid diallyl ester, m.p. 160° C; from 3-nitro-6-chlorobenzaldehyde, acetoacetic acid allyl ester and ammonia.

2,6-dimethyl-4-(α-thienyl)-1,4-dihydropyridine-3,5-dicarboxylic acid diallyl ester, m.p. 119° C; from thiophen-2-aldehyde, acetoacetic acid allyl ester and ammonia.

EXAMPLE 5

1,2,6-Trimethyl-4-(3'-trifluoromethyl-phenyl)-1,4-dihydropyridine-3,5-dicarboxylic acid dipropargyl ester After heating 10 g 3-trifluoromethyl-benzaldehyde, 16 cc acetoacetic acid propargyl ester and 5 g methylamine hydrochloride in 30 cc pyridine for 2 to 3 hours, the mixture is poured into water, filtered off with suction and washed with water; 14 g of pale yellow crystals of m.p. 92° C (methanol).

The following compounds were prepared in an analogous manner from the reactants specified:

a. 1,2,6-trimethyl-4-(4'-carbomethoxyphenyl)-1,4-dihydropyridine-3,5-dicarboxylic acid diallyl ester, m.p. 128° C; from 4-carbomethoxy benzaldehyde, acetoacetic acid allyl ester and methylamine hydrochloride.

b. 1,2,6-trimethyl-4-(3-fluorophenyl)-1,4-dihydropyridine-3,5-dicarboxylic acid diallyl ester, m.p. 68° C; from 3-fluorobenzaldehyde, acetoacetic acid allyl ester and methylamine hydrochloride.

c. 1,2,6-trimethyl-4-(2'-chlorophenyl)-1,4-dihydropyridine-3,5-dicarboxylic acid difurfuryl ester, m.p. 103° C; from 2-chlorobenzaldehyde, acetoacetic acid furfuryl ester and methylamine hydrochloride.

d. 1,2,6-trimethyl-4-(3',4',5'-trimethoxyphenyl)-1,4-dihydropyridine-3,5-dicarboxylic acid dipropargyl ester, m.p. 163° C; from 3,4,5-trimethoxybenzaldehyde, acetoacetic acid propargyl ester and methylamine hydrochloride.

EXAMPLE 6

In a manner analogous to that of Example 4, the following compounds were prepared from the reactants specified:

a. 2,6-dimethyl-4-(4'-nitrophenyl)-1,4-dihydropyridine-3,5-dicarboxylic acid dipropargyl ester, m.p. 137° C; from 4-nitrobenzaldehyde, acetoacetic acid propargyl ester and ammonia.

b. 2,6-dimethyl-4-(3'-nitrophenyl)-1,4-dihydropyridine-3,5-dicarboxylic acid diallyl ester, m.p. 132° C; from 3-nitrobenzaldehyde, acetoacetic acid allyl ester and ammonia.

c. 2,6-dimethyl-4-(2'-nitrophenyl)-1,4-dihydropyridine-3,5-dicarboxylic acid diallyl ester, m.p. 106° C; from 2-nitrobenzaldehyde, acetoacetic acid propargyl ester and ammonia.

d. 2,6-dimethyl-4-(2'-nitrophenyl)-1,4-dihydropyridine-3,5-dicarboxylic acid dipropargyl ester, m.p. 132° C; from 2-nitrobenzaldehyde, acetoacetic acid propargyl ester and ammonia.

e. 2,6-dimethyl-4-(2'-trifluoromethylphenyl)-1,4-dihydropyridine-3,5-dicarboxylic acid dipropargyl ester, m.p. 133°; from 2-trifluoromethylbenzaldehyde, acetoacetic acid propargyl ester and ammonia.

f. 2,6-dimethyl-4-(2'-trifluoromethylphenyl)-1,4-dihydropyridine3,5-dicarboxylic acid diallyl ester, m.p. 111°; from 2-trifluoromethylbenzaldehyde, acetoacetic acid allyl ester and ammonia.

g. 2,6-dimethyl-4-(2'-methoxyphenyl)-1,4-dihydropyridine-3,5-dicarboxylic acid diallyl ester, m.p. 88°; from 2-methoxybenzaldehyde, acetoacetic acid ally ester and ammonia.

h. 2,6-dimethyl-4-(3',4'-dioxymethylene-6'-bromophenyl)-1,4-dihydropyridine-3,5-dicarboxylic acid dipropargyl ester m.p. 145°; from 3,4-dioxymethylene-6-bromobenzaldehyde, acetoacetic acid propargyl ester and ammonia.

i. 2,6-dimethyl-4-(4'-carboxyphenyl)-1,4-dihydropyridine-3,5-dicarboxylic acid dipropargyl ester, m.p. 209°; from 4-carboxybenzaldehyde, acetoacetic acid propargyl ester and ammonia.

j. 2,6-dimethyl-4-(α-pyrrolyl)-1,4-dihydropyridine-3,5-dicarboxylic acid dipropargyl ester, m.p. 210°; from pyrrol-2-aldehyde, acetoacetic acid propargyl ester and ammonia.

k. 2,6-dimethyl-4-(α-N-methylpyrrolyl)-1,4-dihydropyridine-3,5-dicarboxylic acid dipropargyl ester, m.p. 148°; from N-methylpyrrol-2-aldehyde, acetoacetic acid propargyl ester and ammonia.

l. 2,6-dimethyl-4-(4',6'-dimethoxy-5'-pyrimidyl)-1,4-dihydropyridine-3,5-dicarboxylic acid diallyl ester, m.p. 174°; from 4,6-dimethoxypyrimidine-5-aldehyde, acetoacetic acid ethyl ester and ammonia.

m. 2,6-dimethyl-4-(2'-trifluoromethylphenyl)-1,4-dihydropyridine-3,5-dicarboxylic acid difurfuryl ester, m.p. 120°; from 2-trifluoromethylbenzaldehyde, acetoacetic acid furfuryl ester and ammonia.

EXAMPLE 7

In a manner analogous to that of Example 5, the following compounds were prepared from the reactants specified:

a. 1,2,6-trimethyl-4-(3',4'-dioxymethylene-6'-nitrophenyl)-1,4-dihydropyridine-3,5-dicarboxylic acid dipropargyl ester, m.p. 135°; from 3,4-dioxymethylene-6-nitrobenzaldehyde, acetoacetic acid propargyl ester and methylamine hydrochloride.

b. 1,2,6-trimethyl-4-(3',4'-dioxymethylene-6'-bromophenyl)-1,4-dihydropyridine-3,5-dicarboxylic acid diallyl ester, m.p. 103°; from 3,4-dioxymethylene-6-nitrobenzaldehyde, acetoacetic acid allyl ester and methylamine hydrochloride.

c. 1,2,6-trimethyl-4-(2'-nitrophenyl)-1,4-dihydropyridine-3,5-dicarboxylic acid dipropargyl ester, m.p. 127°; from 2-nitrobenzaldehyde, acetoacetic acid propargyl ester and methylamine hydrochloride.

d. 1,2,6-trimethyl-4-(2'-nitrophenyl)-1,4-dihydropyridine-3,5-dicarboxylic acid diallyl ester, m.p. 78°; from 2-nitrobenzaldehyde, acetoacetic acid allyl ester and methylamine hydrochloride.

e. 1,2,6-trimethyl-4-(3'-nitrophenyl)-1,4-dihydropyridine-3,5-dicarboxylic acid diallyl ester, m.p. 82°; from 3-nitrobenzaldehyde, acetoacetic allyl ester and methylamine hydrochloride.

f. 1,2,6-trimethyl-4-(4'-nitrophenyl)-1,4-dihydropyridine-3,5-dicarboxylic acid dipropargyl ester, m.p. 108°; from 4-nitrobenzaldehyde, acetoacetic acid propargyl ester and methylamine hydrochloride.

g. 1,2,6-trimethyl-4-(2'-trifluoromethylphenyl)-1,4-dihydropyridine-3,5-dicarboxylic acid diallyl ester, m.p. 78°; from 2-trifluoromethylbenzaldehyde, acetoacetic acid allyl ester and methylamine hydrochloride.

h. 1,2,6-trimethyl-4-cyclohexyl-1,4-dihydropyridine-3,5-dicarboxylic acid dipropargyl ester, m.p. 79°; from hexahydrobenzaldehyde, acetoacetic acid propargyl ester and methylamine hydrochloride.

i. 1,2,6-trimethyl-4-α-pyrrolyl-1,4-dihydropyridine-3,5-dicarboxylic acid dipropargyl ester, m.p. 188°; from pyrrol-2-aldehyde, acetoacetic acid propargyl ester and methylamine hydrochloride.

j. 1-benzyl-2,6-dimethyl-4-phenyl-1,4-dihydropyridine-3,5-dicarboxylic acid diallyl ester, m.p. 93°; from benzaldehyde, acetoacetic acid allyl ester and benzylamine or benzylamine hydrochloride.

What is claimed is:

1. A compound of the formula:

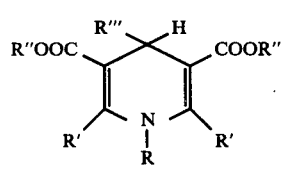

wherein

R is hydrogen, alkyl of 1 to 4 carbon atoms or benzyl;

R' is alkyl of 1 to 4 carbon atoms;

R" is alkenyl of 3 or 4 carbon atoms or alkinyl of 3 or 4 carbon atoms; and

R'" is cyclohexyl; phenyl unsubstituted or substituted by 1 to 3 groups selected from the group consisting of nitro, chlorine, bromine, 1 to 3 methoxy moieties, trifluoromethyl, carbomethoxy, carboxy and 1 or 2 hydroxymethylene moieties; pyridyl; thienyl; pyrrolyl; N-methylpyrrolyl; and dimethoxypyrimidyl.

2. A compound according to claim 1 wherein R'" is alkenyl of 3 or 4 carbon atoms.

3. A compound according to claim 1 wherein R" is alkenyl of 3 or 4 carbon atoms.

4. The compound according to claim 2 which is 2,6-dimethyl-4-(α-pyridyl)-1,4-dihydropyridine-3,5-dicarboxylic acid diallyl ester.

5. The compound according to claim 3 which is 2,6-dimethyl-4-(α-pyridyl)-1,4-dihydropyridine-3,5-dicarboxylic acid dipropargyl ester.

6. The compound according to claim 2 which is 1,2,6-trimethyl-4-(β-pyridyl)-1,4-dihydropyridine-3,5-dicarboxylic acid diallyl ester.

7. The compound according to claim 2 which is 1,2,6-trimethyl-4-(α-pyridyl)-1,4-dihydropyridine-3,5-dicarboxylic acid diallyl ester.

8. The compound according to claim 3 which is 1,2,6-trimethyl-4-(α-pyridyl)-1,4-dihydropyridine-3,5-dicarboxylic acid dipropargyl ester.

9. The compound according to claim 3 which is 2,6-dimethyl-4-phenyl-1,4-dihydropyridine-3,5-dicarboxylic acid dipropargyl ester.

10. The compound according to claim 2 which is 2,6-dimethyl-4-(3'-trifluoromethylphenyl)-1,4-dihydropyridine-3,5-dicarboxylic acid diallyl ester.

11. The compound according to claim 3 which is 2,6-dimethyl-4-(3'-nitrophenyl)-1,4-dihydropyridine-3,5-dicarboxylic acid dipropargyl ester.

12. The compound according to claim 2 which is 2,6-dimethyl-4-(3'-nitro-6'-chlorophenyl)-1,4-dihydropyridine-3,5-dicarboxylic acid diallyl ester.

13. The compound according to claim 2 which is 2,6-dimethyl-4-(α-thienyl)-1,4-dihydropyridine-3,5-dicarboxylic acid diallyl ester.

14. The compound according to claim 3 which is 1,2,6-trimethyl-4-(3'-trifluoromethyl-phenyl)-1,4-dihydropyridine-3,5-dicarboxylic acid dipropargyl ester.

15. The compound according to claim 2 which is 1,2,6-trimethyl-4-(4'-carbomethoxyphenyl)-1,4-dihydropyridine-3,5-dicarboxylic acid diallyl ester.

16. The compound according to claim 2 which is 1,2,6-trimethyl-4-(3'-fluorophenyl)-1,4-dihydropyridine-3,5-dicarboxylic acid diallyl ester.

17. The compound according to claim 3 which is 1,2,6-trimethyl-4-(3',4',5'-trimethoxyphenyl)-1,4-dihydropyridine-3,5-dicarboxylic acid dipropargyl ester.

18. The compound according to claim 3 which is 2,6-dimethyl-4-(4'-nitrophenyl)-1,4-dihydropyridine-3,5-dicarboxylic acid dipropargyl ester.

19. The compound according to claim 2 which is 2,6-dimethyl-4-(3'-nitrophenyl)-1,4-dihydropyridine-3,5-dicarboxylic acid diallyl ester.

20. The compound according to claim 2 which is 2,6-dimethyl-4-(2'-nitrophenyl)-1,4-dihydropyridine-3,5-dicarboxylic acid diallyl ester.

21. The compound according to claim 3 which is 2,6-dimethyl-4-(2'-nitrophenyl)-1,4-dihydropyridine-3,5-dicarboxylic acid dipropargyl ester.

22. The compound according to claim 3 which is 2,6-dimethyl-4-(2'-trifluoromethylphenyl)-1,4-dihydropyridine-3,5-dicarboxylic acid dipropargyl ester.

23. The compound according to claim 2 which is 2,6-dimethyl-4-(2'-trifluoromethylphenyl)-1,4-dihydropyridine-3,5-dicarboxylic acid diallyl ester.

24. The compound according to claim 2 which is 2,6-dimethyl-4-(2'-methoxyphenyl)-1,4-dihydropyridine-3,5-dicarboxylic acid diallyl ester.

25. The compound according to claim 3 which is 2,6-dimethyl-4-(3',4'-methylenedioxy-6'-bromophenyl)-1,4-dihydropyridine-3,5-dicarboxylic acid dipropargyl ester.

26. The compound according to claim 3 which is 2,6-dimethyl-4-(4'-carboxyphenyl)-1,4-dihydropyridine-3,5-dicarboxylic acid dipropargyl ester.

27. The compound according to claim 3 which is 2,6-dimethyl-4-(α-pyrrolyl)-1,4-dihydropyridine-3,5-dicarboxylic acid dipropargyl ester.

28. The compound according to claim 3 which is 2,6-dimethyl-4-(α-N-methylpyrrolyl)-1,4-dihydropyridine-3,5-dicarboxylic acid dipropargyl ester.

29. The compound according to claim 2 which is 2,6-dimethyl-4-(4',6'-dimethoxy-5'-pyrimidyl)-1,4-dihydropyridine-3,5-carboxylic acid diallyl ester.

30. The compound according to claim 3 which is 1,2,6-trimethyl-4-(3',4'-methylenedioxy-6'-nitrophenyl)-1,4-dihydropyridine-3,5-dicarboxylic acid dipropargyl ester.

31. The compound according to claim 2 which is 1,2,6-trimethyl-4-(3',4'-methylenedioxy-6'-bromophenyl)-1,4-dihydropyridine-3,5-dicarboxylic acid diallyl ester.

32. The compound according to claim 3 which is 1,2,6-trimethyl-4-(2'-nitrophenyl)-1,4-dihydropyridine-3,5-dicarboxylic acid dipropargyl ester.

33. The compound according to claim 2 which is 1,2,6-trimethyl-4-(2'-nitrophenyl)-1,4-dihydropyridine-3,5-dicarboxylic acid diallyl ester.

34. The compound according to claim 2 which is 1,2,6-trimethyl-4-(3'-nitrophenyl)-1,4-dihydropyridine-3,5-dicarboxylic acid diallyl ester.

35. The compound according to claim 3 which is 1,2,6-trimethyl-4-(4'-nitrophenyl)-1,4-dihydropyridine-3,5-dicarboxylic acid dipropargyl ester.

36. The compound according to claim 2 which is 1,2,6-trimethyl-4-(2'-trifluoromethylphenyl)-1,4-dihydropyridine-3,5-dicarboxylic acid diallyl ester.

37. The compound according to claim 3 which is 1,2,6-trimethyl-4-cyclohexyl-1,4-dihydropyridine-3,5-dicarboxylic acid dipropargyl ester.

38. The compound according to claim 3 which is 1,2,6-trimethyl-4-α-pyrrolyl-1,4-dihydropyridine-3,5-dicarboxylic acid dipropargyl ester.

39. The compound according to claim 2 which is 1-benzyl-2,6-dimethyl-4-phenyl-1,4-dihydropyridine-3,5-dicarboxylic acid diallyl ester.

* * * * *